United States Patent [19]

Matsuyama et al.

[11] Patent Number: 5,326,705
[45] Date of Patent: Jul. 5, 1994

[54] PROCESS FOR PRODUCING OPTICALLY ACTIVE 1,3-BUTANDIOL BY ASYMMETRIC ASSIMILATION

[75] Inventors: Akinobu Matsuyama, Niigata; Yoshinori Kobayashi, Niigata, both of Japan

[73] Assignee: Daicel Chemical Industries, Ltd., Osaka, Japan

[21] Appl. No.: 989,499

[22] Filed: Dec. 10, 1992

Related U.S. Application Data

[63] Continuation of Ser. No. 744,912, Aug. 14, 1991, abandoned.

[51] Int. Cl.$^5$ .............................................. C12P 41/00
[52] U.S. Cl. ...................................... 435/280; 435/822
[58] Field of Search ................................. 435/280, 822

[56] References Cited
FOREIGN PATENT DOCUMENTS 58-204187 11/1983 Japan .
61-191631 8/1986 Japan .
1320997 12/1989 Japan .
3183499 8/1991 Japan .

OTHER PUBLICATIONS

ATCC Catalog, pp. 145 and 245, 1991.
Bull. Chem. Soc. Jpn., 53, 1356–1360 (1980), Murakami S. et al.

*Primary Examiner*—Douglas W. Robinson
*Assistant Examiner*—S. Saucier
*Attorney, Agent, or Firm*—Birch, Stewart, Kolasch & Birch

[57] ABSTRACT

Optically active 1,3-BUTANEDIOL is produced by contacting microorganisms selected from respective groups of specific genuses having an effect of acting on an enantiomeric mixture of 1,3-butanediols and leaving (R)-1,3-butanediol or (S)-1,3-butanediol in enantiomeric mixture, and collecting the remaining optically active (R)-1,3-butanediol or (S)-1,3-butanediol. Optically active 1,3-butanediol can be produced by an economically excellent and convenient means.

7 Claims, No Drawings

PROCESS FOR PRODUCING OPTICALLY ACTIVE 1,3-BUTANDIOL BY ASYMMETRIC ASSIMILATION

This application is a continuation, of application Ser. No. 07/744,912 filed on Aug. 14, 1991, now abandoned.

BACKGROUND OF THE INVENTION

1. Field of the Invention

The present invention concerns a process for producing an optically active 1,3-butanediol and, more particularly, relates to a process for producing an optically active 1,3-butanediol by contacting specific microorganisms or processing products thereof with an enantiomer mixture of 1,3-butanediols and collecting the resulting optically active 1,3-butanediol.

Optically active 1,3-butanediols are important raw materials for synthesizing various medicines, such as antibiotics.

2. Description of the Prior Art

As a process for producing optically active 1,3-butanediols, there has been known, for example, (1) a method of optically resolving chemically synthesized racemic form 1,3-butanediol by using an optical resolving agent (Japanese Patent Laid-Open Sho 61-191631), and (2) a method of asymmetric synthesis from 4-hydroxy-2-butanone by using a Raney nickel catalyst processed with an optically active compound (Japanese Patent Laid-Open Sho 58-204187 and Bull. Chem. Soc. Jpn., 53, 1356–1360 (1980)) or the like. However, since there are drawbacks to these methods in that expensive optical resolving agents and catalysts have to be used in both methods (1) and (2), as well as in that the optical purity is low in method (2), it has been desired to establish a process capable of obtaining an optically active 1,3-butanediol of high optical purity with an economically excellent and convenient means.

OBJECT AND SUMMARY OF THE INVENTION

The present inventors have invented a process for using microorganisms in a process for obtaining an optically active 1,3-butanediol at high optical purity by an economically excellent and convenient method and, as a result of search for microorganisms suitable to this purpose, have found that the object can be attained by:

a process for producing an optically active 1,3-butandiol which comprises treating an enantiomeric mixture of 1,3-butanediols with a microorganism of the genus Aciculonidium, Brettanomyces, Cochliobolus, Corynespora, Dactylium, Echinopodospora, Hamigera, Helminthosporium Nectria and Phialocephala and having an effect capable of acting on said enantiomeric mixture of 1,3-butanediols and leaving (R)-1,3-butanediol or processing products thereof to an enantiomeric mixture of 1,3-butanediol and collecting remaining optically active (R)-1,3-butanediol, as well as by:

a process for producing an optically active 1,3-butanediol which comprises treating an enantiomeric mixture of 1,3-butanediols with microorganisms selected from the group consisting of microorganisms belonging to the genus of Ambrosiozyma, Bordetella, Fusarium, Gibberella, Glomerella, Gonatobotryum, Neosartorya, Oospora, Paecilomyces, Preussia, Spetoria, Talaromyces and Westerdykella and having an effect capable of acting on said enantiomeric mixture of 1,3-butanediols and leaving (S)-1,3-butanediol or processing products thereof to an enantiomer mixture of 1,3-butanediol and collecting remaining optically active (S)-1,3-butanediol.

The microorganisms usable in the present invention can include any of microorganisms selected from the group consisting of those belonging to the genus of Aciculonidium, Brettanomyces, Cochliobolus, Corynespora, Dactylium, Echinopodospora, Hamigera, Helminthosporium Nectria and Phialocephala and having an effect capable of acting on an enantiomer mixture of 1,3-butanediol and leaving (R)-1,3-butanediol, or microorganisms selected from the group consisting of those belonging the genus of Ambrosiozyma, Bordetella, Fusarium, Gibberella, Glomerella, Gonatobotryum, Neosartorya, Oospora, Paecilomyces, Preussia, Spetoria, Talaromyces and Westerdykella and having an effect capable of acting on an enantiomer mixture of 1,3-butandiol and leaving (S)-1,3-butanediol.

Specifically, as the organisms having an effect capable of acting on the enantiomer mixture of 1,3-butanediols and leaving (R)-1,3-butanediol, there can be mentioned, for example, *Aciculoconidium aculeatum* IFO 10124, *Bretianomyces anomalus* IFO 0796, *Cochliobolus miyabeanus* IFO 6631, *Corynespora cassiicola* IFO 6724, *Dactylium dentroides* ATCC 46032, *Echinopodospora jamaicensis* IFO 9819, *Hamigera avellanea* IFO 7721, *Helminthosporium sigmoideum* var. irregulare IFO 5273, *Nectria cinnabarina* IFO 6821 and *Phialocephala bactrospora* IFO 8770.

Further, as the organisms having an effect capable of acting on the enantiomer mixture of 1,3-butanediols and leaving (S)-1,3-butanediols, there can be mentioned, for example, *Ambrosiozyma monospora* IFO 1965, *Ambrosiozyma philentoma* IFO 1847, *Bordetella bronchiseptica* IFO 13691, *Fusarium oxysporum* IFO 7152, *Fusarium solani* IFO 5232, *Gibberella fujikoroi* IFO 5268, *Glomerella cingulata* IAM 8050, *Gonatobotryum apiculatum* IFO 9098, *Neosartorya fischeri* var. spinosa IFO 5955, *Oospora astringenes* IFO 7001, *Paecilomyces variotii* IFO 4855, *Preussia terricola* IFO 7893, *Spetoria glycines* IFO 5294, *Talaromyces flavus* var. flavus IFO 7231 and *Westerdykella multispora* IFO 5813.

Microorganisms in any form of strains such as wild strain, variant strain and recombinant strain derived by a genetic method such as cell fusion or gene manipulation can be used suitably.

Microorganisms listed with an IFO No. are listed in List of Cultures, eighth addition, vol. 1 (1988) published from Foundation of Institution for Fermentation (IFO) and are available from IFO. Microorganisms listed with an ATCC No. are listed in Catalogue of Bacteria Phages rDNA Vectors, 16th edition (1985) published from American Type Culture Collection (ATCC) and available from ATCC. Microorganisms listed with an IAM No. are available from Institute of Applied Microorganisms of Tokyo University.

There is no particular restriction on the medium used for the culture of microorganisms in the present invention so long as the medium can grow microorganisms. For instance, any carbon sources that can be utilized by the above-mentioned microorganisms can be used and, specifically, there can be mentioned saccharides, such as glucose, fructose, sucrose and dextrin, alcohols such as sorbitol, ethanol and glycerol, organic acids such as fumaric acid, citric acid, acetic acid and propionic acids and salts thereof, hydrocarbons such as paraffin or mixtures thereof. As a nitrogen source, organic or inorganic nitrogen-containing compounds such as, for example, the ammonium salt of an inorganic acid such as ammonium chloride, ammonium sulfate and ammonium phosphate, ammonium salts of organic acids such as ammonium fumarate and ammonium citrate, meat extracts, yeast extract, cone steep liquor, casein hydrolysis product and urea or a mixture thereof. In addition, nutrient sources usually used for culturing microorganisms such as inorganic salts, micro metal salts, vitamins and so on can be properly mixed and used. Further, if required, factors for promoting the growth of microorganisms, factors for increasing the performance of forming the desired compound in the present invention, or substances for effecting a medium pH, can also be added.

Referring to the culturing method, cultivation is conducted with a medium pH of 3.0 to 9.5, preferably, 4 to 8, at a culturing temperature of 20° to 45° C., preferably, 25° to 37° C. under aerophobic or aerobic condition and under the conditions suitable to the growth of the microorganisms for 5 to 120 hours, preferably, about 12 to 72 hours.

As a method of forming an optically active 1,3-butanediols from an enantiomer mixture of 1,3-butanediol, there is a method, for example, of using a culture solution as it is and adding a mixture of an enantiomeric of 1,3-butanediols to the culture solution, a method of separating cells, for example, by centrifugation and re-suspending them as they are or, after washing, into a buffer solution or water, to which an enantiomeric mixture of 1,3-butanediols is added, and reacted. Upon reaction, it may be sometimes advantageous to add a carbon source, such as glucose or sucrose, as an energy source. Further, cells may be used as intact cells or used after undergoing processing such as pulverization, acetone treatment or freeze drying. Further, such cells or cell processing products can be used in an immobilized state by a known method, for example, polyacrylamide gelation, sulfur-containing saccharide gelation (carrageenan gelation method), an alginic acid gelation method and an agar gelation method. Furthermore, enzymes obtained by purification from the cell processing products by combined known methods may also be used.

The enantiomeric mixture of 1,3-butanediols may be used as it is, or being dissolved in water, or in such an organic solvent as giving no effect on the reaction, or dispersed in a surface active agent. It may be added continuously from the first of the reaction, or added portion-wise.

The reaction is conducted within a pH range of 3 to 10, preferably 5 to 9, at a temperature range of 10° to 60° C., preferably 20° to 40° C., for about 1 to 120 hours with or without stirring. When the reaction time is prolonged, although the residual amount of 1,3-butanediol is reduced, an optically active 1,3-butanediol at high optical purity can be obtained. There is no particular restriction on the concentration of the substrate used and it is preferably about 0.1 to 10%.

The optically active 1,3-butanediol remaining and formed by the reaction can easily be collected directly from the reaction solution or after the separation of cells, by a usual purification method, such as extraction with organic solvent, distillation or column chromatography.

EXAMPLE

The present invention will now be explained more specifically referring to examples but the present invention is not restricted only to said examples.

In the examples, 1,3-butanediol in the reaction solution can be easily determined quantitatively by gas chromatography (column: Thermon 3000 (2 m), temperature at 130° C.). The optical purity was measured after acetylating the optically active 1,3-butanediol obtained by reaction with acetyl chloride by a customary method and by high speed liquid chromatography using an optical resolution column (column: a chiral cell OB manufactured by Daicel Chemical Industry Co., solvent: n-hexane/2-propnanol=19:1, wavelength 220 nm and flow rate: 0.5 ml/min) (retention time; 15 min for (S) form, 19.3 min for (R) form).

| Yeast extract | 0.3% |
|---|---|
| Peptone | 0.5% |
| 1,3-butanediol | 0.5% |
| $K_2HPO_4$ | 0.1% |
| $MgSO_4.7H_2O$ | 0.05% |
| pH: | 7.2 |

100 ml of the cell preparation medium described above was placed in a 500 ml volume Sakaguchi flask and, after sterilization, the microorganisms shown in Table 1 were inoculated respectively and cultured under shaking at 30° C. for 48 hours. Subsequently, the cells were separated centrifugally, and washed once with physiological saline to obtain vial cells.

Then, 50 ml of distilled water was charged into a 500 ml volume Sakaguchi flask, to which the above-mentioned vial cells were suspended and 0.5 g of a racemic form of 1,3-butanediol was added and reacted under reciprocal shaking at 30° C. for 48 hours.

After the reaction was over, cells were removed centrifugally and after saturation with sodium chloride, the resultant supernatants, were extracted by using 50 ml of ethyl acetate. Then, the ethyl acetate layer was analyzed on gas chromatography to measure the amount of the remaining 1,3-butanediol.

Then, after dehydrating the ethyl acetate with anhydrous sodium sulfate, it was removed with solvent to obtain a syrup which was then acetylated with acetyl chloride by a customary method and then dissolved into a solvent and analyzed on high speed liquid chromatography. The absolute arrangement and the optical purity of the resultant 1,3-butanediol were measured.

The results obtained are shown in Table 1.

TABLE 1

| Microorganisms | Amount of 1,3-butane diol remained (mg/ml) | Absolute arrangement | Optical purity of 1,3-butane diol (% e.e.) |
|---|---|---|---|
| Aciculoconidium aculeatum IFO 10124 | 6.8 | R | 72 |
| Bretianomyces anomalus IFO 0796 | 4.4 | R | 32 |
| Cochliobolus miyabeanus IFO 6631 | 7.5 | R | 20 |
| Corynespora cassiicola IFO 6724 | 7.6 | R | 26 |
| Dactylium dentroides ATCC 46032 | 7.2 | R | 50 |
| Echinopodospora jamaicensis IFO 9819 | 5.0 | R | 41 |
| Hamigera avellanea IFO 7721 | 4.3 | R | 24 |
| Helminthosporium sigmoideum var. irregulare IFO 5273 | 1.2 | R | 22 |
| Nectria cinnabarina IFO 6821 | 4.7 | R | 27 |
| Phialocephala bactrospora IFO 8770 | 3.7 | R | 36 |

TABLE 1-continued

| Microorganisms | Amount of 1,3-butane diol remained (mg/ml) | Absolute arrangement | Optical purity of 1,3-butane diol (% e.e.) |
|---|---|---|---|
| Ambrosiozyma monospora IFO 1965 | 4.1 | S | 29 |
| Ambrosiozyma philentoma IFO 1847 | 3.4 | S | 83 |
| Bordetella bronchiseptica IFO 13691 | 4.5 | S | 31 |
| Fusarium oxysporum IFO 7152 | 3.3 | S | 98 |
| Fusarium solami IFO 5232 | 0.8 | S | 99 |
| Gibberella fujikoroi IFO 5268 | 6.8 | S | 42 |
| Glomerella cingulata IAM 8050 | 4.6 | S | 87 |
| Gonatobotryum apiculatum IFO 9098 | 6.7 | S | 49 |
| Neoartorya fischeri var. spinosa IFO 5955 | 1.1 | S | 85 |
| Oospora astringenes IFO 7001 | 4.0 | S | 68 |
| Paecilomyces variotii IFO 4855 | 5.5 | S | 67 |
| Preussia terricola IFO 7893 | 5.0 | S | 23 |
| Spetoria glycines IFO 5294 | 4.5 | S | 52 |
| Talaromyce flavus var. flavus IFO 7231 | 1.2 | S | 81 |
| Westerdykella multispora IFO 5813 | 6.6 | S | 44 |

The process for producing an optically active 1,3-butanediol using microorganisms according to the present invention enables an optically active 1,3-butanediol to be easily produced at a high optical purity, and it has high industrial advantage.

What is claimed is:

1. A process for producing an optically active 1,3-butanediol, comprising treating an enantiomeric mixture of 1,3-butanediols with a microorganism selected from the group consisting of *Aciculoconidium aculeatum*, *Brettanomyces anomalus*, *Cochliobolus miyabeanus*, *Corynespora cassiicola*, *Dactylium dentroides*, *Echinopodospora jamaicensis*, *Hamigera avellanea*, *Helminthosporium sigmoideum*, *Nectria cinnabarina*, and *Phialocephala bactrospora*, and which is capable of catabolizing (S)-1,3-butanediol in said enantiomeric mixture of 1,3-butanediols, and recovering optically active (R)-1,3-butanediol.

2. A process according to claim 1, wherein said microorganism is selected from the group consisting of *Aciculoconidium aculeatum* IFO 10124, *Brettanomyces anomalus* IFO 0796, *Cochliobolus miyabeanus* IFO 6631, *Corynespora cassiicola* IFO 6724, *Dactylium dentroides* ATCC 46032, *Echinopodospora jamaicensis* IFO 9819, *Hamigera avellanea* IFO 7721, *Helminthosporium sigmoideum* var. irregulare IFO 5273, *Nectria cinnabarina* IFO 6821, and *Phialocephala bactrospora* IFO 8770.

3. The process according to claim 1, wherein said microorganism is selected from the group consisting of *Aciculoconidium aculeatum* IFO 10124, *Brettanomyces anomalus* IFO 0796, *Cochliobolus miyabeanus* IFO 6631, *Corynespora cassiicola* IFO 6724, *Echinopodospora jamaicensis* IFO 9819, *Hamigera avellanea* IFO 7721, *Helminthosporium sigmoideum* var. irregulare IFO 5273, *Nectria cinnabarina* IFO 6821, and *Phialocephala bactrospora* IFO 8770.

4. A process for producing an optically active 1,3-butanediol, comprising treating an enantiomeric mixture of 1,3-butanediols with a microorganism selected from the group consisting of *Ambrosiozyma monospora*, *Ambrosiozyma philentoma*, *Bordetella bronchiseptica*, *Fusarium oxysporum*, *Fusarium solani*, *Gibberella fujikoroi*, *Glomerella cingulata*, *Gonatobotryum apiculatum*, *Neosartorya fischeri*, *Oospora astringenes*, *Paecilomyces variotti*, *Preussia terricola*, *Spetoria glycines*, *Talaromyces flavus*, and *Westerdykella multispora*, and which is capable of catabolizing (R)-1,3-butanediol from said enantiomeric mixture of 1,3-butanediol, and recovering (S)-1,3-butanediol.

5. A process according to claim 4, wherein said microorganism is selected from the group consisting of *Ambrosiozyma monospora* IFO 1965, *Ambrosiozyma philentoma* IFO 1847, *Bordetella bronchiseptica* IFO 13691, *Fusarium oxysporum* IFO 7152, *Fusarium solani* IFO 5232, *Gibberella fujikoroi* IFO 5268, *Glomerella cingulata* IAM 8050, *Gonatobotryum apiculatum* IFO 9098, *Neosartorya fischeri* var. spinose IFO 5955, *Oospora astringenes* IFO 7001, *Paecilomyces variotii* IFO 4855, *Preussia terricola* IFO 7893, *Spetoria glycines* IFO 5294, *Talaromyces flavus* var. flavus IFO 7231, and *Westerdykella multispora* IFO 5813.

6. The process according to claim 4, wherein said microorganism is selected from the group consisting of *Ambrosiozyma monospora* IFO 1965, *Ambrosiozyma philentoma* IFO 1847, *Bordetella bronchiseptica* IFO 13691, *Fusarium oxysporum* IFO 7152, *Gonatobotryum apiculatum* IFO 9098, *Neosartorya fischeri* var. spinosa IFO 5955, *Oospora astringenes* IFO 7001, *Paecilomyces variotti* IFO 4855, *Preussia terricola* IFO 7893, *Spetoria glycines* IFO 5294, *Talaromyces flavus* var. flavus IFO 7231, and *Westerdykella multispora* IFO 5813.

7. The process according to claim 5, wherein said microorganism is *Glomerella cingulata* IAM 8050.

* * * * *